(12) United States Patent
Dixon et al.

(10) Patent No.: US 6,828,092 B1
(45) Date of Patent: Dec. 7, 2004

(54) IN VIVO ASSAYS FOR MODULATORS OF STEROL BIOSYNTHESIS

(75) Inventors: Graham Keith Dixon, Congleton (GB); Peter Michael Broad, Congleton (GB); David John Scanlon, Wilmslow (GB)

(73) Assignee: Astrazeneca UK Limited, London (GB)

( * ) Notice: Subject to any disclaimer, the term of this patent is extended or adjusted under 35 U.S.C. 154(b) by 1134 days.

(21) Appl. No.: 08/981,964

(22) PCT Filed: Jul. 9, 1996

(86) PCT No.: PCT/GB96/01623

§ 371 (c)(1),
(2), (4) Date: Jan. 12, 1998

(87) PCT Pub. No.: WO97/03202

PCT Pub. Date: Jan. 30, 1997

(30) Foreign Application Priority Data

Jul. 12, 1995 (GB) .............................................. 9514184

(51) Int. Cl.$^7$ .............................. C12Q 1/68; C12N 1/15
(52) U.S. Cl. ................. 435/6; 435/254.11; 435/254.21; 435/254.22; 536/23.2
(58) Field of Search ............................... 435/6, 254.11, 435/254.21, 254.22; 536/23.2

(56) References Cited

U.S. PATENT DOCUMENTS

| | | | |
|---|---|---|---|
| 5,168,040 A | 12/1992 | Ryan et al. ..................... | 435/6 |
| 5,378,603 A | 1/1995 | Brown et al. .................. | 435/6 |
| 5,569,588 A | 10/1996 | Ashby et al. .................. | 435/6 |
| 5,580,722 A | 12/1996 | Foulkes et al. ................ | 435/6 |
| 5,776,675 A | 7/1998 | Broad ........................... | 435/6 |
| 5,777,888 A | 7/1998 | Rine et al. ................... | 364/496 |
| 5,846,720 A | 12/1998 | Foulkes et al. ................ | 435/6 |

FOREIGN PATENT DOCUMENTS

| | | |
|---|---|---|
| EP | 0 626 453 A1 | 11/1994 |
| EP | 0 627 491 A1 | 12/1994 |
| EP | 627 491 | * 12/1994 |
| WO | WO 94/09126 | 4/1994 |

OTHER PUBLICATIONS

M. Servouse et al. "Regulation of Early Enzymes of Ergosterol Biosynthesis in Saccharomyces cerevisiae", Biochem J. 240: 541–547, 1986.*

S. Dequin et al., "Cloning, Sequencing and Analysis of the Yeast S. uvarum ERG10 Gene Encoding Acetoacetyl CoA Thiolase", Curr. Genet. 13: 471–478, 1988.*

Hiser et al., ERG10 from Saccharomyces cerevisiae Encodes Acetoacetyl–CoA Thiolase, The Journal of Biological Chemistry, vol. 269, No. 50, pp. 31383–31389, 1994.

Hiser et al., Sequence Listing of ERG10, Mar. 11, 1995 Swiss Prot. Acc. #SCAACOAT.

Servouse et al., Regulation of early enzymes of ergosterol biosynthesis . . . , The Biochemical Journal, vol. 240, No. 2, pp. 541–547, 1986.

Trocha et al., Location and Regulation of Early Enzymes of Sterol Biosynthesis in Yeast, Archives of Biochemistry and Biophysics, vol. 174, No. 1, pp. 45–51, 1976.

Dequin et al., Effect of Acetoacetyl CoA Thiolase Amplification on Sterol Synthesis in the Yeasts S. Cerevisiae and S. Uvarum, Biotechnology Letters, vol. 10, No. 7, pp. 457–462, 1988.

Servouse et al., Isolation and Characterization of Yeast Mutants Blocked in Mevalonic Acid Formation, Biochemical and Biophysical Research Communications, Vo. 123, No. 2, pp. 424–430, 1984.

Dimster–Denk et al., Transcriptional Regulation of a Sterol–Biosynthetic Enzyme by Sterol Levels in Saccharomyces cerevisiae, Molecular and Cellular Biology, vol. 16, No. 8, pp. 3981–3989, 1996.

Dixon et al., A Reporter Gene Assay for Fungal Sterol Biosynthesis Inhibitors, J. Steroid Biochem. Molec. Biol., vol. 62, No. 2/3, pp. 165–171, 1997.

* cited by examiner

*Primary Examiner*—Rebecca E. Prouty
(74) *Attorney, Agent, or Firm*—Fish & Richardson P.C.

(57) ABSTRACT

A method for the identification of agents which modulate sterol biosynthesis which method comprises contacting a test compound with a host cell comprising a DNA sequence which controls expression of a yeast acetoacetyl CoA thiolase gene operably linked to a reporter system such that modulation of sterol biosynthesis in the host cell leads to a detectable change in cell phenotype, and determining whether any such detectable change has occurred.

12 Claims, 11 Drawing Sheets

FIG. 6

Flutriafol

SEQUENCE LISTING

```
<160> NUMBER OF SEQ ID NOS: 4

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Candidate
      binding site for dimeric DNA binding protein

<400> SEQUENCE: 1
cgtggccagg                                                          10

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 2
ggaggtcgac aaactacttc attgacatgg                                    30

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 3
ggagaagctt ggactcgagt acgtctaatc tgtataaat                          39

<210> SEQ ID NO 4
<211> LENGTH: 554
<212> TYPE: DNA
```

```
<213> ORGANISM: Artificial Sequence
<220> FEATURE:
<223> OTHER INFORMATION: Description of Artificial Sequence: Partial
      sequence of S. cerevisiae acetoacetyl CoA thiolase
      (AcoAT)

<400> SEQUENCE: 4
gtcgacaaac tacttcattg acatggaatc tgctaaagat ttgaagtatt tctgtgagat      60
gattattttc gagaaacttg atcgattaaa gaagaatcct tacgcacata agccctttgg    120
ttctacaaga ggtcacctct catcttcgag aagaagattg cgtacataat ctacgatata    180
tcctgtaaat agaaacagct acactgcttg aaagccttaa catgatacat ttctggtatg    240
atgccattgt tgtgccctgc cgggtttatc gtttcctaac aggcacgtca cttataacga    300
ggtgcctgtc gtttaccgcc caagccggtt ttttcgctgg agagtacggt actactagcc    360
caccacacgt tcgtggccag gttgataggc caccgttgag caaagggcag taaaatatat    420
aaaagaggaa caagcgcttc cattaagagc actgctaagc ctactcgttt tctagttctc    480
tgaaaaaagg tagcctaaaa caagcgccat atcatatata tttatacaga ttagacgtac    540
tcggatccaa gctt                                                       554
```

IN VIVO ASSAYS FOR MODULATORS OF STEROL BIOSYNTHESIS

This application is the national phase of international application PCT/GB96/01623 filed Jul. 9, 1996 which designed the U.S.

The present invention relates to a method for identifying compounds which modulate sterol biosynthesis. In particular the invention provides in vivo assays for inhibitors of sterol biosynthesis wherein inhibition leads to a change in the level of expression of a reporter gene. The invention also relates to nucleic acids and recombinant cells for use in the above assays.

Two general approaches may be taken to the identification of inhibitors of a metabolic pathway. In the first approach, one or more individual enzymes from the pathway are selected, and compounds are screened for their ability to inhibit these enzymes in in vitro reactions. This approach can be labour intensive, and, depending on the assay and enzymes used, expensive. An alternative approach is to construct a system which reports on the activity of the entire metabolic pathway, either by directly measuring the levels of the product of the pathway, or by using an indirect measurement of these levels. In both prokaryotes and eukaryotes the products of a metabolic pathway sometimes regulate the expression of the genes which encode the enzymes in the pathway. By coupling the regulatory regions of these genes to reporter genes it is possible to obtain reporter gene assays for inhibitors of metabolic pathways.

In mammalian cells, the product of sterol biosynthesis (cholesterol) regulates the transcription of the genes encoding 3-hydroxy-3-methylglutaryl coenzyme A (HMG-CoA) synthase and HMG-CoA reductase. The sequences within the promoter regions of these genes which mediate the regulation of transcription in response to sterols have been determined, and are referred to as sterol response elements (SREs: Brown and Goldstein (1990) Nature 343, 425–430). A transcription factor which binds to these sequences has been characterised, and a mechanism for sterol regulation of the activity of this factor, involving sterol-regulated proteolysis, has been proposed (Wang et al (1994) Cell 77, 53–62). Construction of sterol-responsive reporter genes using SRE sequences has been described. For example, in mammalian cells, additional of exogenous sterols inhibits sterol biosynthesis and will also inhibit the activity of SRE-driven reporter genes (Osborne et al (1985) Cell 42, 203–212).

The regulation of genes encoding enzymes in fungal sterol biosynthesis is less well characterised. No sequence element equivalent to the SRE has been defined. HMG-CoA reductase is subject to feedback regulation by sterol levels in the budding yeast *Saccharomyces cerevisiae* (*S. cerevisiae*), but this regulation occurs at the translational level and is mediated by the 5' untranslated region of the HMG1 mRNA (Dimster-Denk et al (1994) Mol. Biol. Cell 5, 655–665). Limited studies have been performed which examine the activities of other enzymes in the sterol biosynthetic pathway in the *S. cerevisiae* under conditions which inhibit ergosterol production. Squalene synthase levels are increased 2–3 fold by application of the HMG-CoA reductase inhibitor lovastatin (Robinson et al (1993) Mol. Cell Biol. 13, 2706–2717), and squalene epoxidase activity can increase up to 5 fold in mutant yeast strains containing limited sterol amounts. Messenger RNA levels of lanosterol 14-a-demethylase accumulate during anaerobic growth (Turi and Loper (1992) J. Biol. Chem. 267, 2046–2052); induction of this gene forms the basis for a patent application by Kirsch (EP 0627 491 A1) for a screen for inhibitors of ergosterol biosynthesis. This screen, which also requires additional manipulation of the yeast to reduce flux through the sterol biosynthetic pathway (by deletion of the HMG1 gene), only appears to detect compounds acting on lanosterol 14-a-demethylase or further down the sterol biosynthesis pathway. For example, tolnaftate, an inhibitor of squalene monooxygenase, was not detected in this screen (Kirsch, p. cit.).

We have now devised a assay which is capable of detecting a wide range of inhibitors of sterol biosynthesis. In this assay inhibition of ergosterol synthesis results in the induction of reporter gene activity in a yeast tester strain. The assay is simple, cheap and robust and may be employed in high throughput mode to screen large chemical collections, natural product collections and compound libraries. Sterol biosynthesis inhibitors have a number of applications. As inhibitors of an essential process in eukaryotes they are useful as antifungal drugs and agrochemicals, and may also have applications as biocides and as antiparasitic agents. In humans, cholesterol may be synthesised de novo or absorbed from the intestine. Inhibition of de novo synthesis reduces lipid levels in the bloodstream, resulting in reduced risk, of atherosclerosis. Sterol biosynthesis provides metabolic intermediates which are used in lipid modification (farnesylation and geranylgeranylation) of proteins. Inhibition of the early stages of sterol biosynthesis may indirectly inhibit lipid modification. This may be of therapeutic application, for example in inhibiting tumour growth driven by activated ras genes.

Therefore in a first aspect of the present invention we provide a method for the identification of agents which modulate sterol biosynthesis which method comprises contacting a test compound with a host cell comprising a DNA sequence which controls expression of a yeast acetoacetyl CoA thiolase (ACoAT) gene operably linked to a reporter system such that modulation of sterol biosynthesis in the host cell leads to a detectable change in cell phenotype, and determining whether any such detectable change has occurred.

By "operably linked" we mean linked in such a way as to provide the basic sequence signals necessary for initiation of gene transcription and initiation of gene translation.

By "a DNA sequence which controls expression" we mean a sequence which confers responsiveness of the activity of adjacent genes to change(s) in intracellular metabolic pathways such as sterol biosynthesis. In general such sequences are protein binding sites. Such proteins may regulate events such as transcriptional activation. Their ability to perform this regulation may be influenced by intracellular processes which feedback from sterol biosynthesis.

Acetoacetyl-CoA thiolase (EC 2.3.1.9) catalyses the condensation of two acetyl-CoA molecules to acetoacetyl-CoA. This enzyme precedes HMG-CoA synthase in the sterol biosynthetic pathway. There have been no studies of the regulation of the expression of this gene, and only limited studies on the regulation of the enzyme activity. ACoAT activity can be repressed 12 fold by addition of exogenous sterol (Trocha and Sprinson, Arch. Biochem. Biophys. (1976) 174, 45–51). Servouse and Karst (Biochem. J. (1986) 240, 541–547) provide similar evidence, showing that ergosterol starvation increases ACoAT activity, whereas ergosterol excess reduces ACoAT activity. These studies examined enzyme activities rather than the expression of the ACoAT gene, and thus it is not possible to determine whether the regulation is due to alterations in the enzyme itself, such as covalent modifications, or the binding of a modulator molecule, or whether the level of the protein is regulated through control of gene expression. The ACoAT gene was cloned from the brewing yeast *Saccharomyces uvarum* (Dequin et al (1988) Curr. Genet. 13, 471–478). These authors report that this gene is highly expressed. Furthermore, overexpression of this gene did not lead to an increase in ergosterol production, leading Dequin et al to conclude that ACoAT is not a rate-limiting enzyme in the production of ergosterol. Despite the availability of DNA probes which could be used to measure mRNA levels under different conditions, no studies of the expression of the ACoAT gene in fungi have been conducted under conditions of ergosterol depletion through anaerobic, mutant or inhibitor conditions. We have found that when the promoter region of *S. cerevisiae* acetoacetyl CoA thiolase is linked to a reporter gene the reporter gene may be induced by sterol biosynthesis inhibitors. This assay provides a convenient, cheap and robust screen for novel inhibitors of sterol biosynthesis.

Fungal species which may be useful in either the provision of an acetoacetyl-CoA thiolase promoter, or which may provide a host cell suitable for use in the construction of a reporter gene assay, include Saccharomyces species such as *Saccharomyces cerevisiae* and *Saccharomyces uvarum*, *Schizosaccharomyces pombe*, Candida species, *Cryptococcus neoformans, Histoplasma capsulatum, Pneumocystis carinii, Neurospora crassa*, Septoria species, *Magnaporthe grisea*, Aspergillus species, Ustilago species and *Botrylis cinerea*.

The assay may be potentially used to detect inhibitors of any of the enzymes involved in fungal sterol biosynthesis. These enzymes include acetoacetylCoA thiolase, HMG-CoA synthase, HMG-CoA reductase, mevalonate kinase, mevalonate-5-phosphate kinase, mevalonate-5-phosphate decarboxylase, squalene synthase, squalene epoxidase, 2,3-oxidosqualene cyclase, C24-methyltransferase, C14-demethylase, D14-reductase, D8-7 isomerase, C5-desaturase and C24(28)reductase. Although the assay is established in fungal cells, inhibitors of mammalian enzymes involved in sterol biosynthesis may be identified either through the ability of compounds to inhibit both the fungal and mammalian homologues of a particular enzyme, or through use of fungal cells engineered to express a mammalian enzyme from the sterol biosynthesis pathway.

In a preferred aspect of the present invention inhibitors of sterol biosynthesis lead to reporter system activation. The advantage of using a reporter gene as a reporter system is that it confers a readily measurable phenotype upon the cell. The reporter gene may conveniently comprise the coding sequence of a enzyme such as *E. coli* β-galactosidase (Casadaban et al., (1983) Meth. Enzymol. 100, 293–308), firefly luciferase (de Wet et al.,(1987) Mol. Cell Biol. 7, 725–737), or *E. coli* choramphenicol acetyl transferase (Gorman et al., (1982) Mol. Cell Biol. 2, 1044–1051), or green fluorescent protein, in which the phenotype conferred may be measured by alterations in fluorescence (Chalfie et al., (1994) Science 263, 802–805).

Alternatively the reporter system may comprise a gene essential for the growth of the cell, for example a gene encoding an essential metabolic enzyme. In this case, activation of the gene will allow cell growth. Alternatively the reporter gene may encode an enzyme which metabolises a toxic substrate. In the presence of this substrate, activation of the reporter gene will again allow growth of the cell. Therefore in a further aspect of the invention we provide an assay for agents which modulate sterol biosynthesis in which the output is the growth of the reporter cell.

The assay described here may be used in combination with another reporter system in the same cell, allowing for compounds to be simultaneously screened for the ability to modulate sterol biosynthesis and other processes. The recent disclosure of novel forms of green fluorescent proteins with different absoption spectra allows the use of multifunctional assays in the cell using the same output (Delagrave et al (1995) Bio/Technology 13, 151–154).

The reporter gene assays may be performed in a variety of ways. In Example 1 we describe the use of liquid reporter gene assays in microtitre plates. Assays may also be performed on solid media in indicator plates, in which positive compounds may appear as zones of colour, the size of the zone being a measure of the potency of the compound. Such zone screening approaches may be particularly applicable to the use of the reporter assay in screening combinatorial libraries or compounds synthesised on solid media (Ecker and Crooke (1995) Bio/Technology 13, 351–360).

In a further aspect of the invention we provide reporter cells containing the ACoAT-based reporter gene which may also contain mutations or other additional genes which alter the rate of flux through the sterol biosynthesis pathway and hence alter the sensitivity of the assay to sterol biosynthesis inhibitors. We also provide cells which contain mutations, such as cell wall mutations, which increase the permeability of the fungal cell wall to compounds and other exogenous agents. Such mutations may be selected by mutagenising a reporter strain such as that described in Example 1, and selecting cells which show an enhanced reponse to sterol biosynthesis inhibitors.

In a further aspect of the invention we provide cells which contain the reporter system, and which also contain genes encoding enzymes of the sterol biosynthesis pathway from other organisms. It may be desirable to express such genes in combination with disruptions and/or mutations of host genes. For example, the host gene encoding a certain enzyme may be disrupted and a gene encoding the homologous human enzyme introduced. Compounds which are active against the "humanised" reporter strain, but inactive against the parental strain containing the fungal homologue of the enzyme, are likely to be acting by inhibiting the human form of this enzyme.

In the example below we describe the construction of an *S. cerevisiae* strain in which the reporter gene is integrated into the host genome. Various alternative methods of maintaining reporter genes in fungal cells include the use of multicopy and single copy episomal plasmids.

In the reporter strain described in Example 1, in which the promoter of an acetoactyl CoA thiolase gene is linked to a reporter gene, inhibition of sterol biosynthesis results in stimulation of reporter gene output. This reporter gene output allows further definition of the promoter elements which mediate the response to reductions in sterol levels. There are at least two ways in which such information could lead to the construction of more sensitive screens for sterol biosynthesis inhibitors:

(1) yeast promoter regions can be quite complex, containing binding sites for multiple proteins, some of which may act as activators of gene expression, and some of which may act as repressors of gene expression (reviewed by Struhl (1989) Ann. Rev. Biochem. 58, 1051–1077 and Curr. Opin. Cell Biol. (1993) 5, 513–520). The definition of activator and repressor regions by construction of deletion mutants would allow the construction of synthetic promoters in which the repressor regions had been removed. This could enhance reporter gene output in response to sterol biosynthesis inhibition and may increase the sensitivity of the screen.

(2) the definition of an element which mediates the effect of sterol biosynthesis inhibition on reporter gene activation could lead to the development of new improved promoters based on this element. For example, the *S. cerevisiae* GAL1 gene was found to inducible by galactose (St. John and Davis (1981) J. Mol. Biol. 152, 285–315). The galactose responsive region was mapped by deletion analysis (West et al (1984) Mol. Cell Biol. 4, 2467–2478). Within this region, four homologous sequences were found to be binding sites for the transcription factor GAL4 (Giniger et al (1985) Cell 40, 767–774). Comparison of these sequences led to the deduction of a consensus binding site for GAL4, and has allowed the synthesis of related sites which do not occur naturally but which are strong binding sites for GALA (Marmorstein et al (1992) Nature 356, 408–414). With this knowledge of the GAL4-DNA interaction it has been possible to construct synthetic promoters which are highly responsive to GALA by either multimerising the number of GALA binding sites, or using strong binding sites. In a similar way, elements in the ACoAT promoter which mediate the effect of sterol biosynthesis inhibition may be binding sites for transcription factors, and systematic mutagenesis of such sequences may lead to the definition of a consensus response element, the multimerisation of which may be used to construct reporter strains which are more sensitive to sterol biosynthesis inhibition. Therefore in a further aspect of the invention we provide reporter cells in which the reporter system is sensitive to sterol biosynthesis inhibition, and in which the promoter for the reporter system contains one or more sequence elements from an ACoAT promoter, or one or more sequence elements derived from analysis of the ACoAT promoter.

Identification of the sterol response element that mediates the effect will allow the cloning of proteins which bind this element. Cloning of such DNA binding proteins may be performed by a variety of methods. cDNA expression libraries may be screened with the appropriate DNA fragment (Singh et al (1988) Cell 52, 415–423). Alternatively, the reporter strain may be subjected to mutagenesis and mutants isolated which lack the reporter gene response. Cloning of genes which complement these mutaions may identify DNA binding proteins (Rose and Broach pp 195–230 of Guide to yeast genetics and moleculr biology (Guthrie and Fink eds.) Meth. Enzymol. vol. 194 (1991) Academic Press). Also, the "one-hybrid" system, involving fusion of cDNA libraries to a transcriptional activator region, may be employed (Wang and Reed (1993) Nature 364, 121–126). Cloning of factors which mediate the sterol responsiveness of the ACoAT gene may lead to the characterisation of the mechanism of feedback regulation of sterol biosynthesis in fungi, and may also elucidate new targets for drug action.

The invention will now be illustrated but not limited by reference to the following detailed description, Example, and Figures:

The *S. cerevisiae* ACoAT gene (ERG 10) has been cloned (Hiser et al (1994) J. Biol. Chem. 269, 31383–31389) and the DNA sequence deposited in the Genbank-EMBL database (Hiser et al Accession no. L20428, 30th Jun. 1994). Hiser et al disclose approximately 500 bp of sequence upstream of the start site of translation of the ACoAT gene. We refer to this region as the 5' flanking region of the ACoAT gene. We have cloned the 5' flanking region region and fused it to a reporter gene (*Escherishia coli* (*E. coli*) b-galactosidase). This gene was introduced into *S. cerevisiae* cells to make a reporter yeast strain. In the reporter strain we find that the activity of the reporter gene when grown under aerobic conditions in the absence of inhibitors of sterol biosynthesis is low. This contrasts with the report of Dequin et al (op. cit.) that the ACoAT gene is highly expressed in *S. uvarum*. After incubation with sterol biosynthesis inhibitors for a period of several hours, reporter gene activity is induced considerably. Up to 9-fold induction can be obtained in this way. Such induction occurs with several compounds which are known to inhibit sterol biosynthesis, including those which act early in sterol biosynthesis (before the sterol nucleus has been formed), and those which act at later steps (after the sterol nucleus has been formed). The induction of reporter gene activity in this yeast reporter strain is useful for screening compound collections for novel inhibitors of sterol biosynthesis. These results also provide evidence that ACoAT activity is feedback regulated by sterol levels at least in part through regulation of gene transcription, and that at least some of the DNA elements which mediate this effect reside within the promoter region used to construct the reporter gene.

The reporter gene was constructed using 5' flanking sequence disclosed in the deposition of Hiser et al. In the deposited sequence of *S. cerevisiae* ACoAT gene, the coding region starts at position 548.The reporter gene described here was constructed from a DNA fragment containing nucleotides 7–543 of this sequence. Several alternative fragments of the gene could have been chosen for construction of the reporter gene. Eukaryotic promoters consist of a number of binding sites for trans-acting factors. The binding of these factors determines both the site at which transcription initiates and the level of transcription from that site. The site of transcription initiation in the ACoAT gene was not mapped by Dequin et al (op. cit.) However, a consensus sequence for a TATA box, TATAAA, is present at position 419–424 and is also present at the homologous position in the *S. cerevisiae* gene. The TATAAA sequence, a binding site for the general transcription factor TFIID, positions the start site of transcription (Nagawa and Fink (1985) Proc. Natl. Acad. Sci. USA 82, 8557–8561; Hahn et al (1985) Proc. Natl. Acad. Sci. USA 82, 8562–8566). Transcription usually initiates betwenn 60 and 120 bp downstream of the TATA box in *S. cerevisiae*. It appears most probable that transcription initiates at around position 490, since this is the location of an "RRYRR" sequence, used as the transcription start site in 45% of *S. cerevisiae* genes analysed (Hahn et al, op. cit.). Thus the fragment of 5' flanking region employed in the construction of the reporter gene in Example 1 was chosen because of the likelihood that it would confer efficient transcriptional initiation together with any regulation by sterol levels. A number of alternative ways of using the 5' flanking region of the ACoAT gene to construct the reporter gene can be envisaged. Fusion points downstream of the translation initiation codon of ACoAT could also be used, but would need to be chosen with care so that the encoded fragment of the thiolase gene is in frame with the reporter gene coding region. Fusion points upstream of that used in Example 1 may also be functional, though if they lack the TATAAA box or regulatory sequences, they may not function as well as the reporter gene described in Example 1. A possible binding site for a transcription factor is located at positions 373–382. This sequence, SEQ ID NO:1 CGTGGCCAGG, is an imperfect inverted repeat which is conserved in the *S. uvarum* promoter region. Inverted repeat structures are potential binding sites for dimeric DNA binding proteins. We also note that some 5' untranslated region of the ACoAT gene is included in the reporter construct, and that effects of sterol biosynthesis inhibitors on reporter gene expression could, in theory, be due effects on mRNA translation mediated by this sequence at the RNA level, rather than by effects on transcription.

The cis-acting sequences which mediate the induction of reporter gene expression in response to sterol biosynthesis could be defined initially by creating deletions of the ACoAT promoter and fusing them to a reporter gene. Some information about potential protein binding sites in the promoter region may be obtained by analysing the sequence for palidromic sequences (which may be binding sites for dimeric DNA binding proteins) and sequences conserved between the promoter regions of other genes. The sequence SEQ ID NO:1 CGTGGCCAGG (positions 372–381 of FIG. 11 SEQ ID NO:4, positions 373–382 of Hiser et al Genbank-EMBL Accession no. L20428)) is a candidate for a binding site for a dimeric DNA binding protein, by virtue of its near-palindromic nature. This sequence is conserved in the promoter of the ACoAT gene from S. uvarum. Furthermore, an 80% match to this sequence is also found in the promoter region of the S. cerevisiae CYC1 gene (positions 171–180 of Genbank Accession no. M11345). In a yeast strain in which the ERG3 (C5 desaturase) gene is deleted, the CYC1 gene is induced 6 fold (Parks and Smith (1995) Yeast 11, S311). In this strain ergosterol biosynthesis is inhibited by the ERG3 gene deletion and this results in induction of the CYC1 gene. It is possible that the induction of CYC1 in the ERG3-deleted strain and reporter gene induction in the reporter strain MEY133::pACoAT by inhibition of sterol biosynthesis occurs by similar mechanisms, in which case the sequence element identified above could play a role. The CYC1 and ACoAT gene share only one other short region of homology within 150 bp upstream of their putative TATA boxes. This region, which is not palindromic, occurs at positions 387–403 of ACoAT (128–144 of CYC1). However, neither this sequence, nor the near palindrome SEQ ID NO:1 CGTGGCCAGG discussed above, are found within the upstream regions of other genes encoding enzymes in the sterol biosynthesis pathway, such as ERG3 (C5 desaturase), ERG1 (squalene monooxygenase), ERG8 (phosphomevalonate kinase) and ERG9 (squalene synthase). Thus, an analysis of promoter regions of genes encoding enzymes of the sterol biosynthesis pathway does not reveal a common sequence element which is likely to be the equivalent of the mammalian sterol response element. It is difficult to predict which regions of the fragment used in construction of the reporter plasmid pACoAT are necessary for the reporter gene response to sterol biosynthesis inhibition. It is likely that the putative TATA box is necessary for accurate transcription initiation. If there is any translational regulation of gene expression, then the 5' noncoding region of the ACoAT mRNA (positions 490–543) is likely to be important. Regulation at the level of transcription initiation would by contrast most likely involve sequences upstream of the TATA box ("upstream activating sequences"; Struhl, op. cit.).

In Example 1 we describe the construction of an S. cerevisiae reporter strain in which the reporter gene is integrated at the ura3 locus. Various alternative modes of constructing and introducing reporter genes into S. cerevisiae will be apparent to the person of ordinary skill. The reporter gene should ideally consist of the 5' flanking region operationally linked to the coding region of a reporter gene. Downstream of the coding region it may be desirable to have a terminator sequence from an S. cerevisiae gene. The reporter gene may be introduced by integration into the host genome, or it may be located on a single or multicopy plasmid. A variety of common laboratory strains of S. cerevisiae may be used to establish the screen, provided that they contain host mutations which allow the introduction and maintenance of foreign DNA. Introduction of mutations in genes encoding enzymes in the sterol biosynthetic pathway may alter the flux through the pathway and alter the signal to noise ratio of the reporter gene in the assay. The introduction of mutations in genes involved in cell wall biosynthesis, or the mating of the reporter strain with strains displaying an enhanced permeability to compounds, may increase the permeability of the reporter strain to compounds which can inhibit sterol biosynthesis and activate the reporter gene. The reporter strain itself may be made more sensitive to compounds by mutagenising the strain and selecting mutants which show enhanced reporter gene output to positive compounds.

Example 1 shows a summary of the compounds used in FIGS. 2–10, the enzymes which they inhibit, the overall level of reporter gene induction at a concentration of 100 µg/ml, and the reporter gene induction per cell at a concentration of 100 µg/ml. Reporter gene induction is defined as:

$$[OD570_{f100} - OD570_{i100}]/[OD570_{f10} - OD570_{i10}]$$

where f refers to a final reading, and i to an initial reading. 100 to a concentration of 100 µg/ml and 10 to a concentration of 10 ng/ml. Reporter gene induction per cell is defined as:

$$[\{OD570_{f100} - OD570_{i100}\}/OD570_{i100}]/[\{OD570_{f10} - OD570_{i100}\}/OD570_{i10}]$$

FIG. 1 summarises the structure of a reporter gene containing 5' flanking sequences from the ACoAT gene. Nucleotides 7–543 of the S. cerevisiae ACoAT gene were obtained as a PCR fragment with a SalI site at the 5' end and a HindIII site at the 3' end. This was inserted between the SalI and HindIII sites of the plasmid pJP 159 to create the plasmid pACoAT. TATA indicates the position of a TATA sequence, a likely binding site for TATA binding protein. The coding region of β-galactosidase is indicated by a shaded region, with ATG marking an initiator methionine. There are 112 bp between the HindIII site and the methionine. The sequence in this region derives from the plasmid pRY171. The numbers derive from the sequence of ACoAT.

FIG. 2 shows dose-responses of reporter gene activity and growth for lovastatin. Reporter gene activity (OD570final–OD570initial) is indicated by solid squares. Growth (OD570 final) is indicated by open squares. Each point is the average of three measurements. Error bars indicate standard deviations.

FIG. 6 shows dose-responses of reporter gene activity and growth for flutriafol. Nomenclature is as in FIG. 2.

Figure 1:
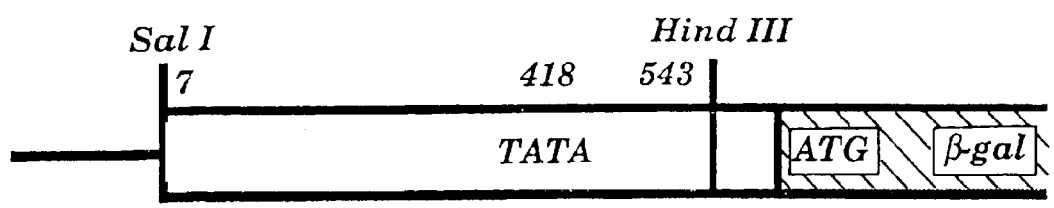
Figure 11:
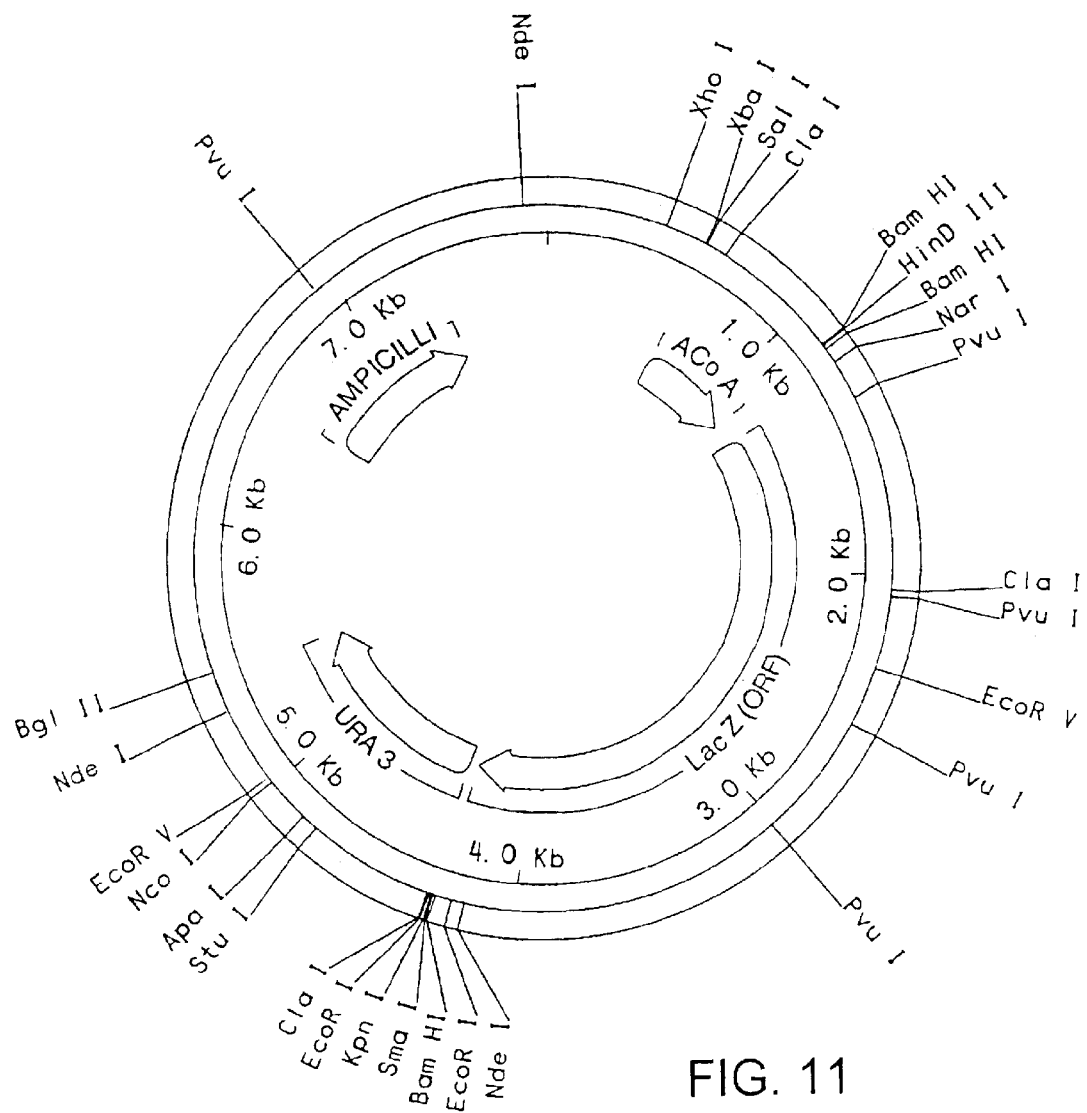

FIG. 11 shows the structure of plasmid pACoAT as referred to in the legend to FIG. 1 and in FIG. 1. The structure of this 7.6 kb plasmid is shown to scale, together with selected restriction enzyme cleavage sites. The open reading frame of E. coli b-galactosidase is located between the HindIII and KpnI sites and is denoted by the arrow marked LacZ(ORF). The S. cerevisiae URA3 gene is located between the KpnI and BglII sites and contains a unique ApaI site used to linearise the DNA for transformation of yeast. Between BglII and XhoI is the backbone of the plasmid, derived from SP72 and containing the Ampicillin resistance gene. Between XhoI and SalI is a terminator from the GAL11 gene. Finally, the ACoAT promoter, as shown in SEQ ID NO:4, is located between the SalI and HindIII sites and is marked by the arrow labelled "ACoA".

EXAMPLE 1

In this example we describe the construction of a reporter gene containing the promoter of the ACoAT gene, the construction of a reporter yeast strain, and set of conditions under which high levels of reporter gene induction can be obtained with sterol biosynthesis inhibitors.

DNA manipulations were performed using standard protocols (Sambrook et al (1989): Molecular Cloning: A Laboratory Manual, 2nd Edition, Cold Spring Harbor Press). Yeast manipulations were also performed according to standard protocols (Guthrie and Fink (1991) Guide to Yeast Genetics and Molecular Biology: Methods in Enzymology, 194, Academic Press; Ausabel et al., (1993) Current Protocols in Molecular Biology (Wiley), Chapter 13). Yeast liquid medium deficient in uracil was prepared as follows. A solution lacking uracil, tryptophan, leucine, histidine and a carbon source was prepared by mixing 7 g Yeast Nitrogen Base without amino acids (Difco 0919-15-3), 85 mls amino acid stock solution(see below), and 400 mls double distilled water. The pH was adjusted to pH 5.4 and the volume made up to 840 mls with water. This solution was then sterilised. To prepare 1 litre of uracil-deficient medium, 100 ms of 20% (w/v) glucose, 20 mls 0.6% (w/v) L-Leucine (filter sterilised), 20 mls 0.2% (w/v) L-tryptophan (filter sterilised) and 20 mls 0.2% (w/v) L-Histidine-HCl (filter sterilised) were then added.

85 ml amino acid stock solution comprised:
20 ml 0.2% (w/v) Adenine Hemisulphate
2 ml 1% (w/v) L-Arginine-HCl
2 ml 1% (w/v) L-Methionine
15 ml 1% (w/v) L-Tyrosine
3 ml 1% (w/v) L-Isoleucine
3 ml 1% (w/v) L-Lysine-HCl
5 ml 1% (w/v) L-Phenylalanine
10 mi 1% (w/v) L-Glutamic acid
10 ml 1% (w/v) L-Aspartic acid
5 ml 3% (w/v) L-Valine
5 ml 4% (w/v) L-Threonine
5 ml 8% (w/v) L-Serine Reporter gene activity assays (β-galactosidase assays) were performed using a single step procedure with the substrate chlorophenol red-β-D-galactopyranoside (CPRG, Boehringer): this substrate gives rise to a red product when cleaved by β-galactosidase. The appearance of this product can assessed by monitoring the optical density at 570 nm (OD570). The assays were performed in the wells of microtitre plates containing 200 μi of yeast in uracil-deficient medium. 50 μl of reaction mix was added to these wells, and immediately after this the absorption at 570 nm was measured using a Molecular Devices plate reader. Reaction mix was prepared as follows. 10×Z buffer (Ausabel et al) was prepared by dissolving 85.2 g $Na_2HPO_4$, 62.4 g $NaH_2PO_4.2H_2O$, 7.5 g KCl and 2.46 g $MgSO_4.7H_2O$ in 500 mls water. 2.7 mls β-mercaptoethanol was added to this solution and mixed. The pH was adjusted to pH 7 using 5M NaOH and the volume made up to 1 litre with water. 200 mls of reaction buffer was made by mixing 100 mls 10×Z buffer, 1.0 ml of 20% (w/v) sodium docedyl sulphate, 10 mls 50 mM CPRG and 89 mls water. After 2 hours a final OD570 reading was taken. Over this time frame, using the yeast strains descibed below, the rate of change of OD570 was constant. Therefore OD570final minus OD570 initial is taken as a measure of total reporter gene activity. OD570 initial is taken as a measurement of the number of cells in the culture, and reporter gene activity per cell is calculated as (OD570initial−OD570final)/OD570initial.

Construction of a Reporter Yeast Strain

A reporter gene in which the E. coli β-galactosidase gene was placed under control of 5' flanking sequences from the S. cerevisiae ACoAT gene was constructed. The structure of this reporter gene is outlined in FIG. 1. The parental plasmid used in this construction was pJP159 (J. Pearlberg, Ph.D. Thesis, Harvard University, 1994; gift of J. Pearlberg). This plasmid contains the following: the backbone of the SP72 plasmid (Promega) allowing propagation in E. coli, the S. cerevisiae URA3 gene to enable selection for transformants in ura3 strains of S. cerevisiae, the GAL1 promoter of S. cerevisiae and the E. coli b-galactosidase gene from the plasmid RY171 (Yocum et al (1984) Mol. Cell Biol. 4, 1985–1998), and a transcription terminator from the S. cerevisiae GAL11 gene (a 0.45 kilobase fragment immediately downstream of the GAL 11 stop codon- Suzuki et al (1988), Mol. Cell Biol., 8, 4991–4999). The reporter plasmid was constructed by replacing the GAL1 region by the 5'flanking region of the S. cerevisia, as outlined below and described in the legend to FIG. 1.

Yeast genomic DNA was prepared from YT6::171 (Himmelfarb et al (1990) Cell 63, 1299–1309) according to the method of Phillipsen et al (1991) Guide to yeast genetics and molecular biology, Chapter 11 (C. Guthrie and G. R. Fink, eds.: Academic Press). The sequence of the S. cerevisiae acetoacetyl CoA thiolase gene was deposited in 1994 in the Genbank-EMBL database by Hiser et al (Accession no. L20428). The translation initation codon is located at position 548 of this sequence. On the assumption that the first 543 bp of this sequence would contain the sequences required for transcription initiation and possibly sequences required for sterol regulation, the following synthetic oligonucleotides were used to amplify by polymerase chain reaction nucleotides 7 to 543 of this sequence from S. cerevisiae genomic DNA.

5'-GGAGGTCGACAAACTACTTCATTGACATGG-3' (SEQ ID NO:2)
5'-GGAGAAGCTTGGATCCGAGTACGTCTAATCTGTA-TAAAT-3' (SEQ ID NO:3)

This amplification was performed on 100 ng genomic DNA using TaqI polymerase (Amplitaq/Perkin-Elmer); annealing at 55° C. for 3 minutes, extension at 74° C. for 5 minutes and denaturation at 92° C. for 2 minutes. 25 cycles of this regime were performed, yielding a DNA fragment of the expected size (0.53 kb). The resultant 0.53 kb DNA fragment, which also contained SalI and HindIII restriction endonuclease cleavage sites provided by the oligonucleotides used for PCR, was digested with those enzymes and inserted between the SalI and HindIII sites of the plasmid pJP159. The insertion of the ACoAT promoter was designed so that the b-galactosidase gene became functionally linked to the promoter. This plasmid was cleaved within the URA3 gene at the ApaI site and transformed into the S. cerevisiae strain MEY133 (Mat a, leu2–3, 112, ura3–52, rme1, trp1, his4) made competent by the lithium acetate method. Transformants were selected for their ability to grow on synthetic complete medium lacking uracil.

The colonies obtained by this procedure were transferred to X-Gal indicator plates to gain an impression of the activity of the reporter gene. Several colonies were grown in uracil-deficient medium and incubated in the presence or absence of terbinafine. A culture in which the reporter gene was induced by terbinafine was selected for further study. This strain is referred to as MEY133::pACoAT. Aliquots of stationary phase culture were stored down in 15% glycerol at −70° C.

Maximal induction of reporter gene activity by terbinafine in MEY133::pACoAT was obtained by:

(1) thawing a 1 ml aliquot of frozen stock and adding it to 100 ml of uracil deficient medium in a 500 ml conical flask and incubating for 24 hours at 30° C. with agitation to aerate the culture.

(2) diluting a sample of this culture with uracil deficient medium to give 100 mls of a culture with an optical density at 600 nm of 1.0 units, and incubating this culture for a further 24 hours in an incubator at 30° C. with agitation.

(3) diluting a sample of this culture with uracil deficient medium to give a culture with an optical density at 600 nm of 0.35 units. This culture was dispensed into 96 well flat-bottomed mucrotitre plates containing compounds. Each well contained 20 µl compound dissolved in 10% (v/v) dimethylsulphoxide. 180 µl culture was added each well. The plates were sealed with Titertex plate sealers and incubated for 24 hours at 30° C.

(4) The plates were removed from the incubator, and shaken to resuspend the yeast. The platesealers were removed and cult reaction mix added to each well. An initial OD570 reading was taken immediately following this addition. After a further two hours a final OD570 reading was taken. Optical density readings were taken with a Molecular Devices platereader using Softmax software. The machine was set to automatically agitate the samples before taking the reading.

The reporter gene in the yeast strain MEY133::ACoAT is induced by a range of sterol biosynthesis inhibitor. FIGS. 2–10 present dose-responses to nine different sterol biosynthesis inhibitors. The measurements of reporter gene activity and growth were obtained using the standard procedure described above. Each point on the graph is the average of three measurements, standard deviations being indicated by the error bars. In the absence of sterol biosynthesis inhibitors, a basal activity of the reporter gene is observed. This corresponds to a change in OD570 of 0.23 units/two hours (average of 15 measurements). During the period of time of the incubation the yeast cells grow to a density of 0.86 OD570 units (average of 15 measurements). These basal measurements are used in calculating the observed level of reporter gene induction (which does not take into account the number of cells present) and the level of reporter gene induction per cell.

Figure 2:
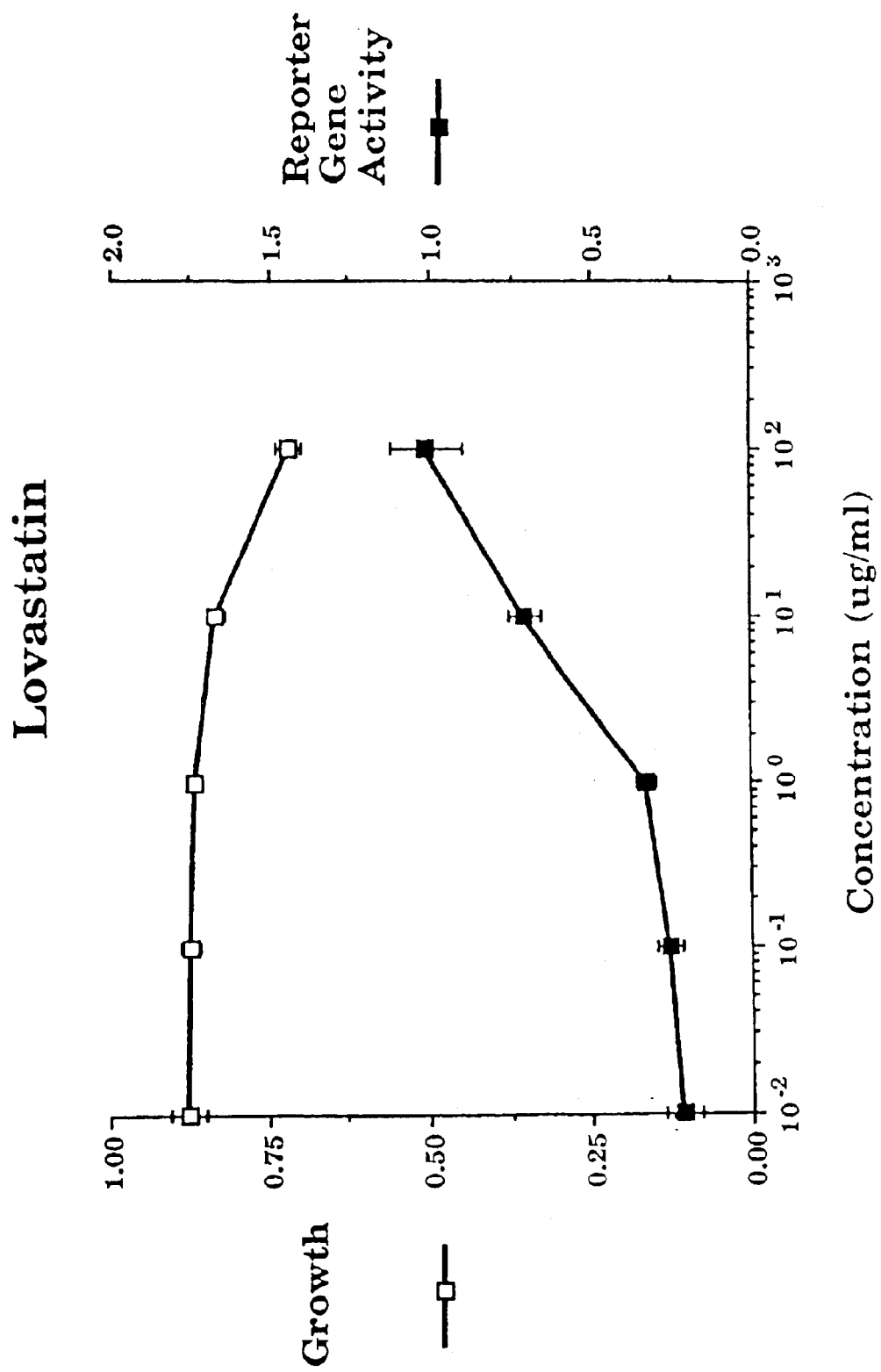

Lovastatin (U.S. Pat. No. 4,231,938 (1980))was obtained from Merck and Co. This compound is an inhibitor of both mammalian and fungal HMG-CoA reductase. This compound induces reporter gene activity at concentrations above 1 µg/ml (FIG. 2).

Figure 3:
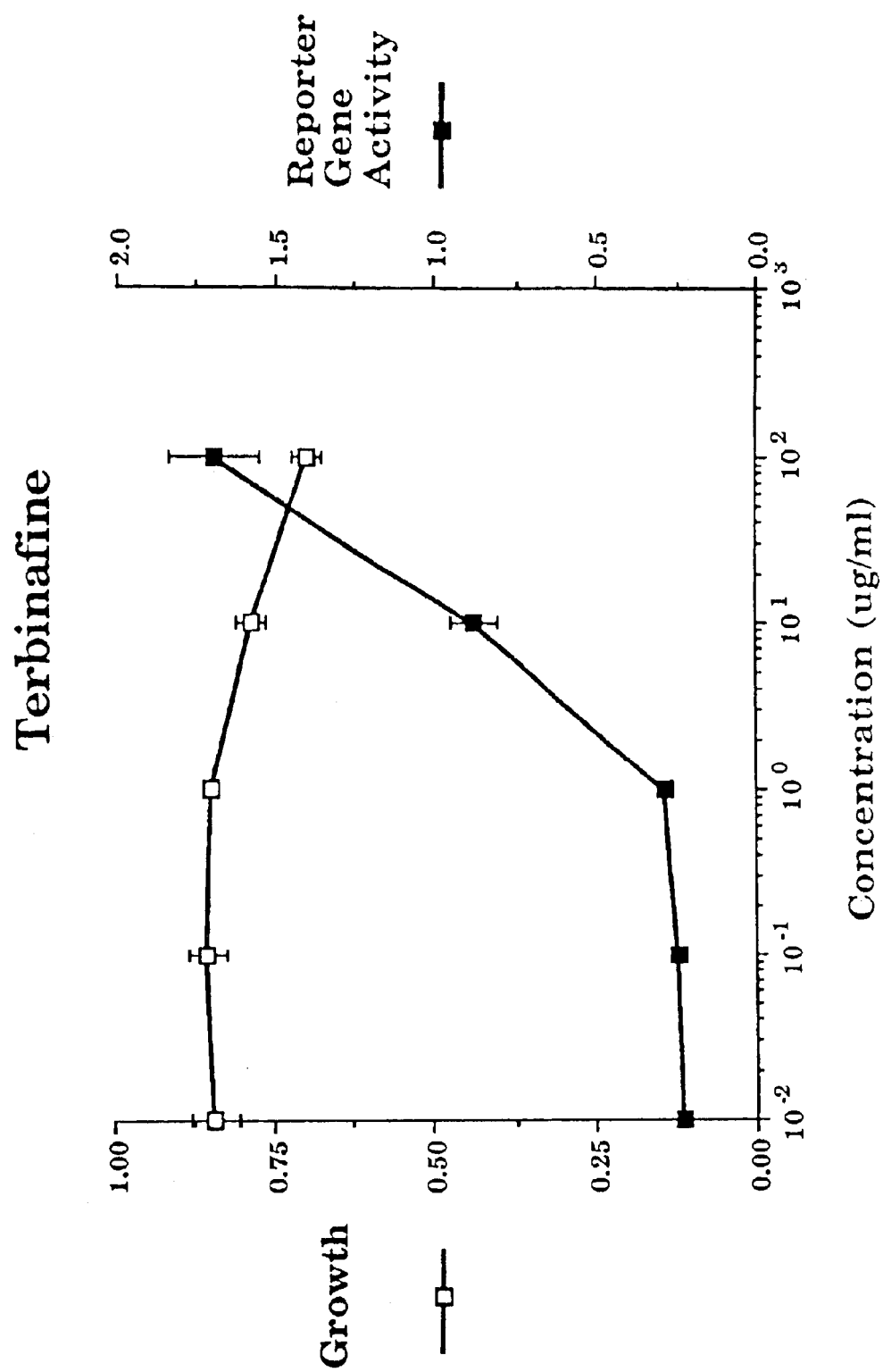
FIG. 3 shows dose-responses of reporter gene activity and growth for terbinafine. Nomenclature is as in FIG. 2.

Terbinafine (EP 24,587 (1981)) was obtained from Sandoz. This compound is a squalene epoxidase inhibitor. This compound inhibits growth to a limited extent, but induces reporter gene activity at concentrations above 1 µg/ml (FIG. 3).

Figure 4:
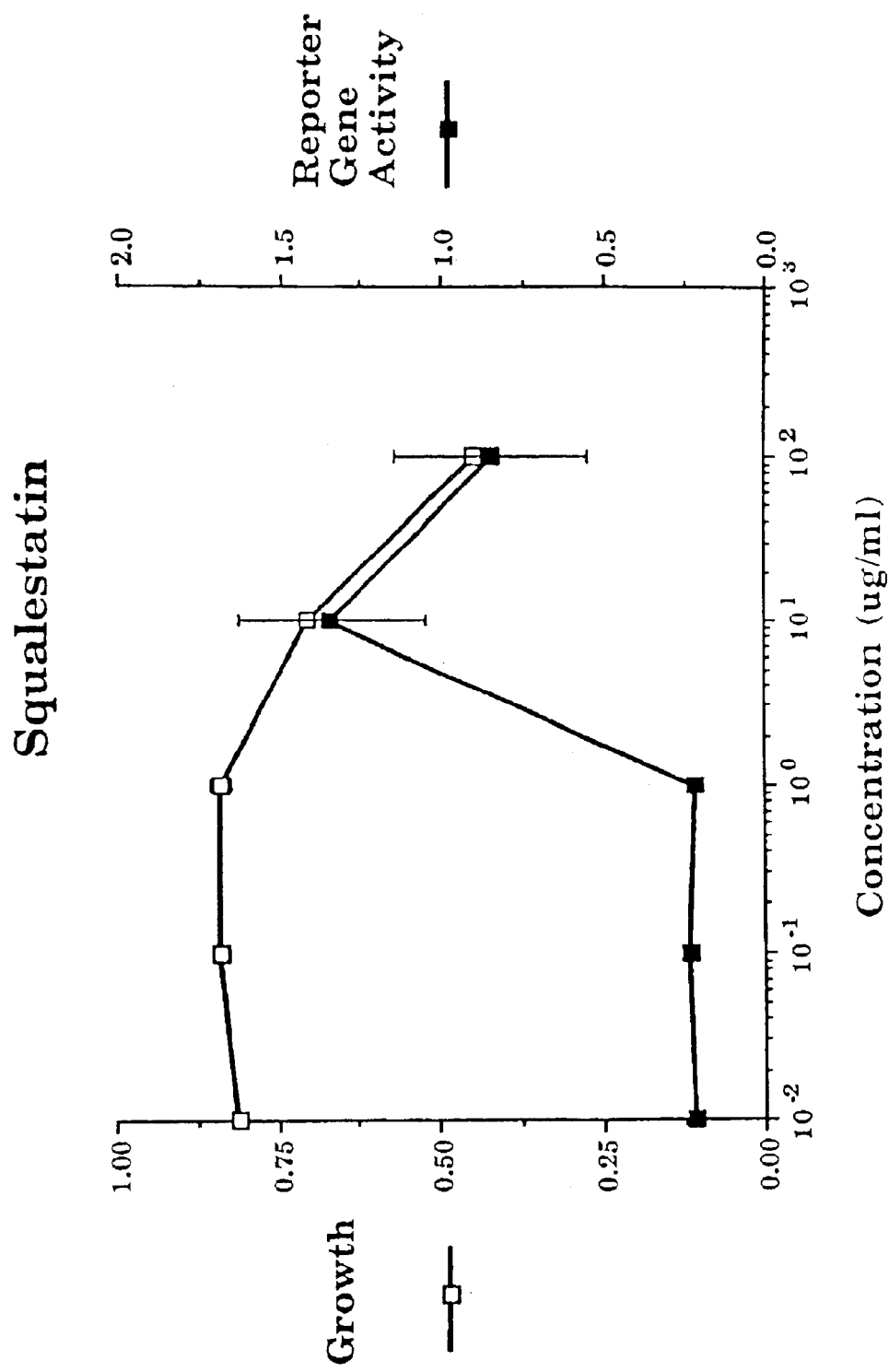
FIG. 4 shows dose-responses of reporter gene activity and growth for squalestatin. Nomenclature is as in FIG. 2.

Squalestatin (Dawson et al (1992) J. Antibiotics 45, 639–647) was obtained from Glaxo. This compound is an inhibitor of squalene synthase. A biphasic response of reporter gene activity to squalestatin was observed (FIG. 4). Maximal reporter gene induction is observed at 10 µg/ml. Above this level, the reporter gene induction decreases. This effect is presumably due to the growth inhibitory effect of squalestatin at higher concentrations. The reporter gene activity per cell is almost identical at 10 µg/ml and 100 µg/ml, indicating the the reporter gene is already maximally induced at 10 µg/ml squalestatin.

Figure 5:
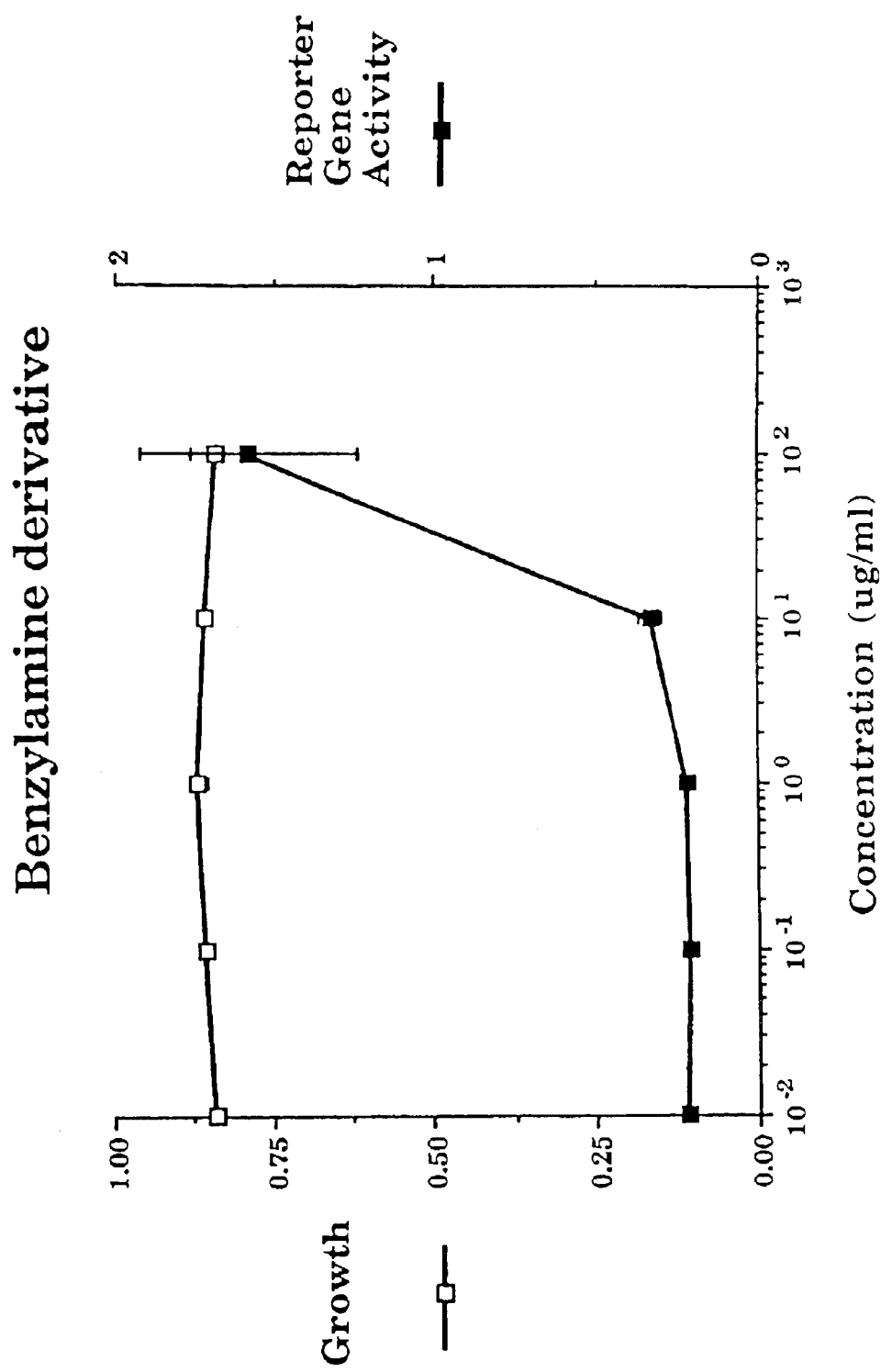
FIG. 5 shows dose-responses of reporter gene activity and growth for 4-t-butyl-N-methyl-N-(1-naphthylmethyl) benzylamine. Nomenclature is as in FIG. 2.
Figure 7:
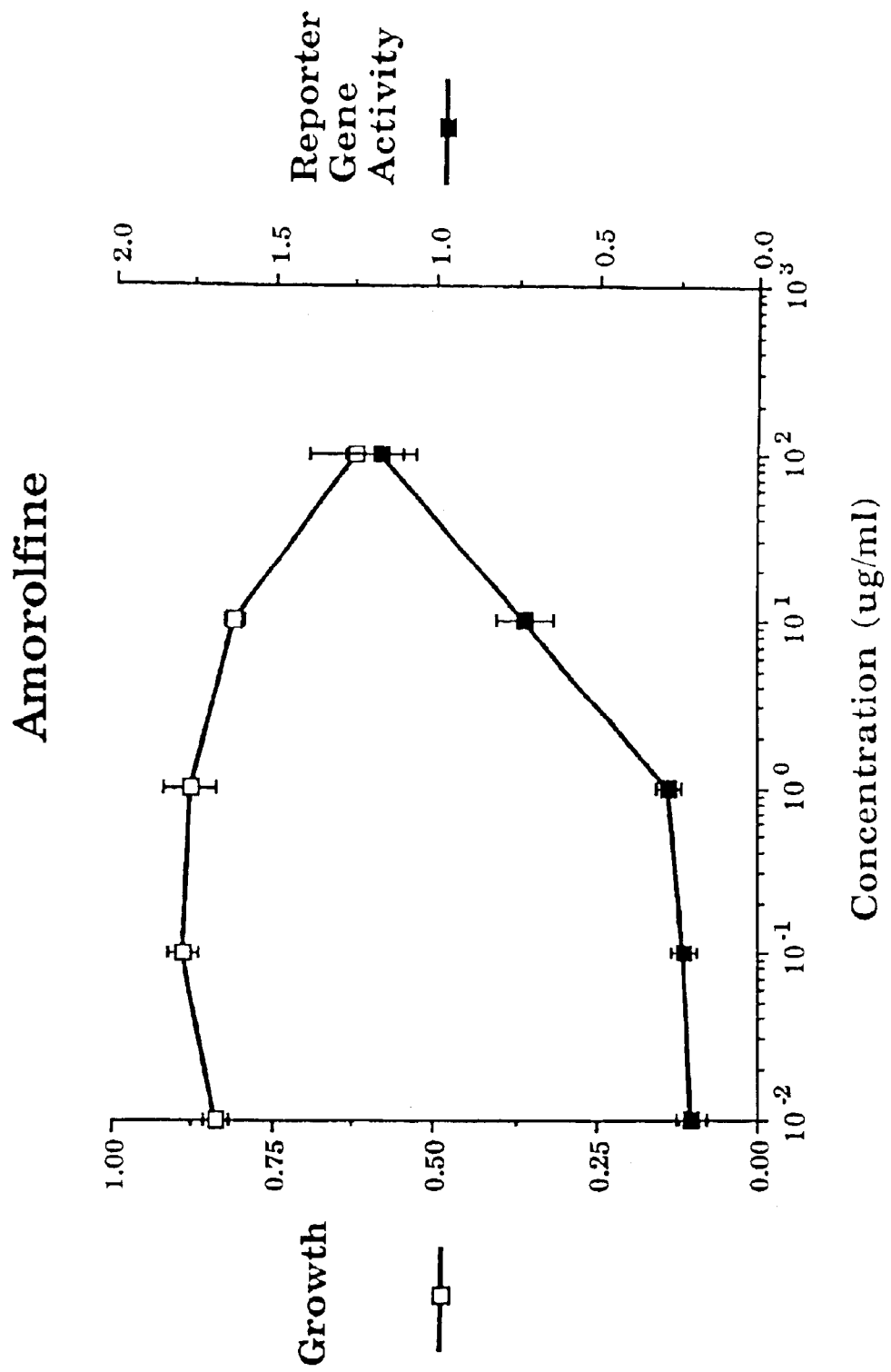
FIG. 7 shows dose-responses of reporter gene activity and growth for amorolfine. Nomenclature is as in FIG. 2.

4-t-butyl-N-methyl-N-(I-naphthylmethyl)benzylamine was made according to the method set out in EP-A-0164697 (Kaken). This is, like terbinafine, a squalene epoxidase inhibitor. It induces reporter gene activity to the same extent as terbinafine at 100 µg/ml, but is much less active than terbinafine at 10 µg/ml (FIG. 5).

Figure 6:
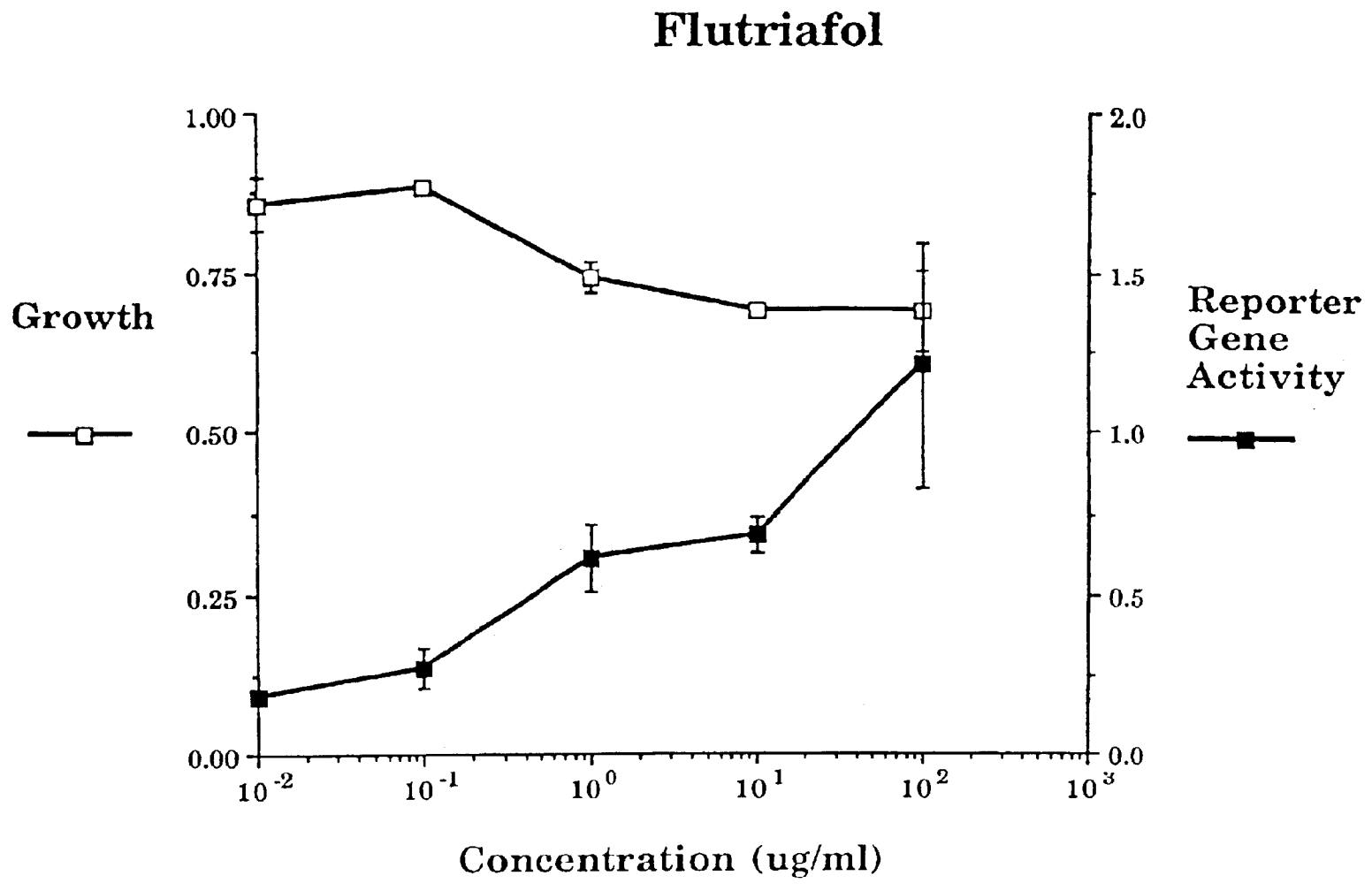

Flutriafol (EP 15,756 (1980)) is a C14-demethylase inhibitor. Some growth inhibition is observed with this compound, and the compound is active a lower doses than the squalene epoxidase and squalene synthase inhibitors, detectable reporter gene induction occurring at 0.1 µg/ml (FIG. 6).

Amorolfine (U.S. Pat. No. 4,202,894 (1980)) is a morpholine inibitor of D8-7 isomerase and was obtained from Hoffman-La Roche. This compound shows some growth inhibitory properties, and induces reporter gene activity above 1 µg/ml (FIG. 6).

Figure 8:
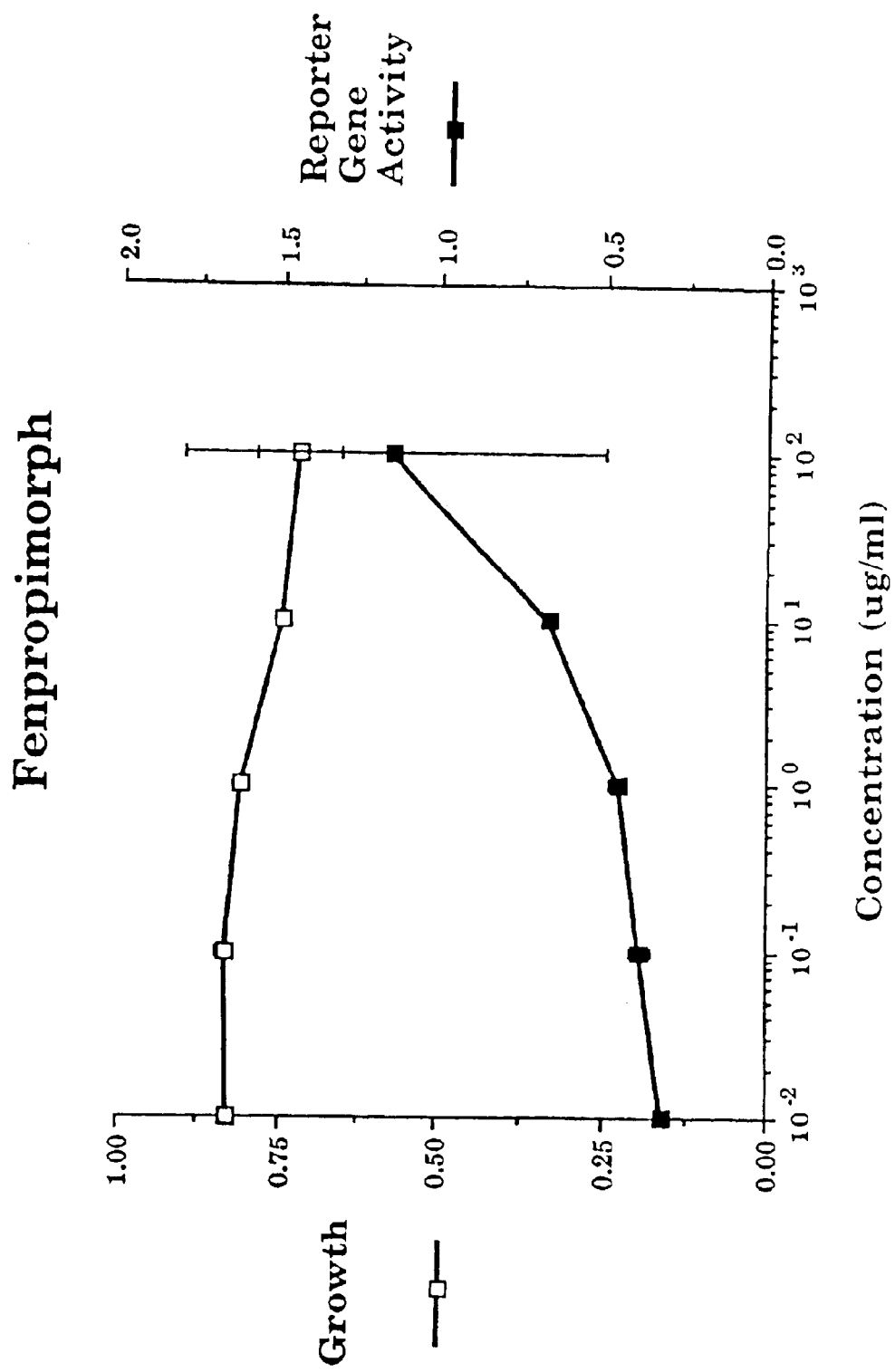
FIG. 8 shows dose-responses of reporter gene activity and growth for fenpropimorph. Nomenclature is as in FIG. 2.

Fenpropimorph (German patent 2,656,747 (1978)), obtained from BASF, is also a D8-7 isomerase inhibitor. Like amorolfine, this compound induces reporter gene activity while also inhibiting growth to some extent (FIG. 8).

Figure 9:
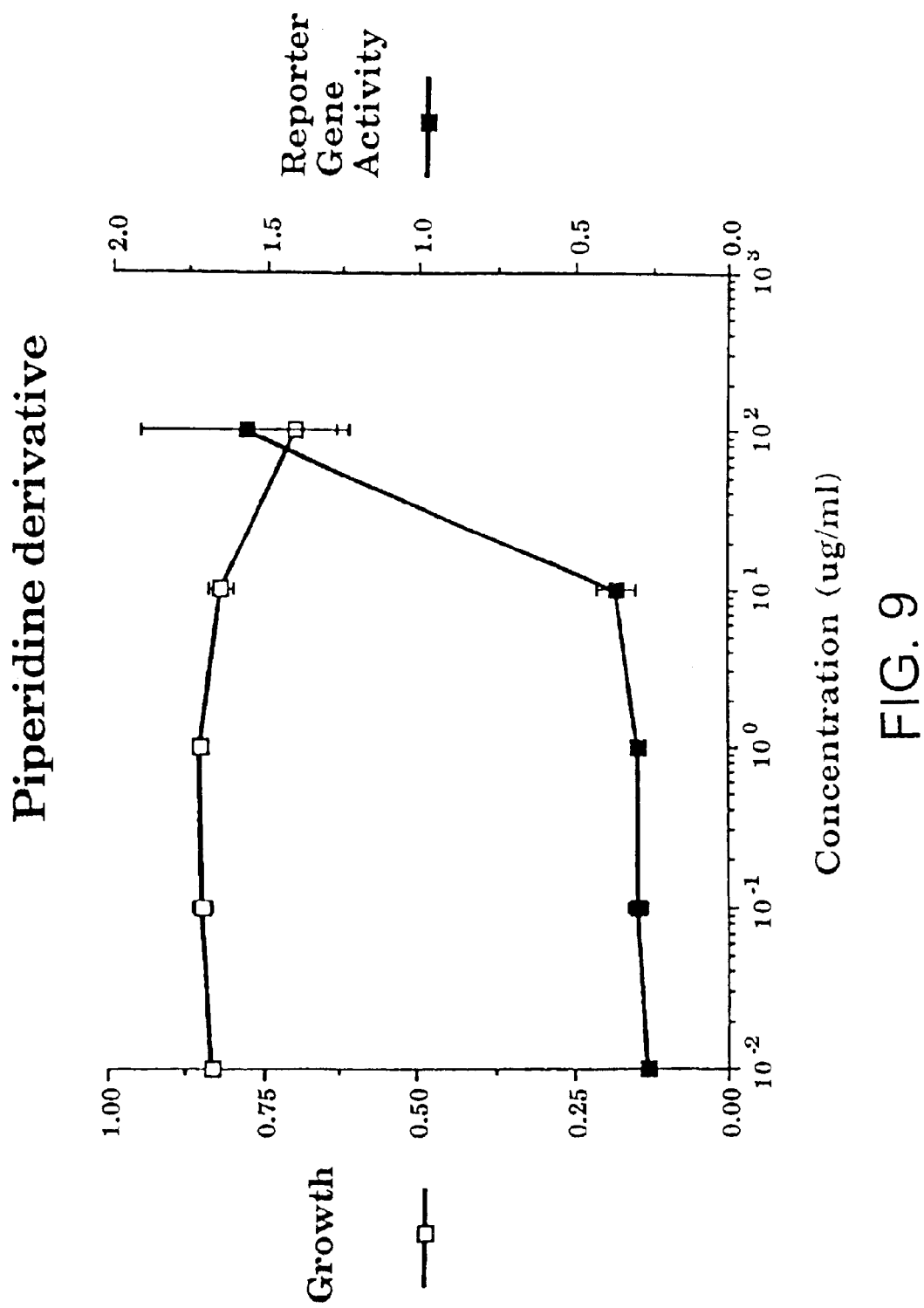
FIG. 9 shows dose-responses of reporter gene activity and growth for 3-(4-t-butylbenzyl)-(N-hexyl)-piperidine. Nomenclature is as in FIG. 2.

3-(4-t-butylbenzyl)-(N-hexyl)-piperidine was synthesised as described in EP-A-0494 717 (Shell). This compound is also a D8-7 isomerase inhibitor. Unlike amorolfine and fenpropimorph, the induction of reporter gene activity is only occurs above 10 µg/ml, and is very sharp (FIG. 9).

Figure 10:
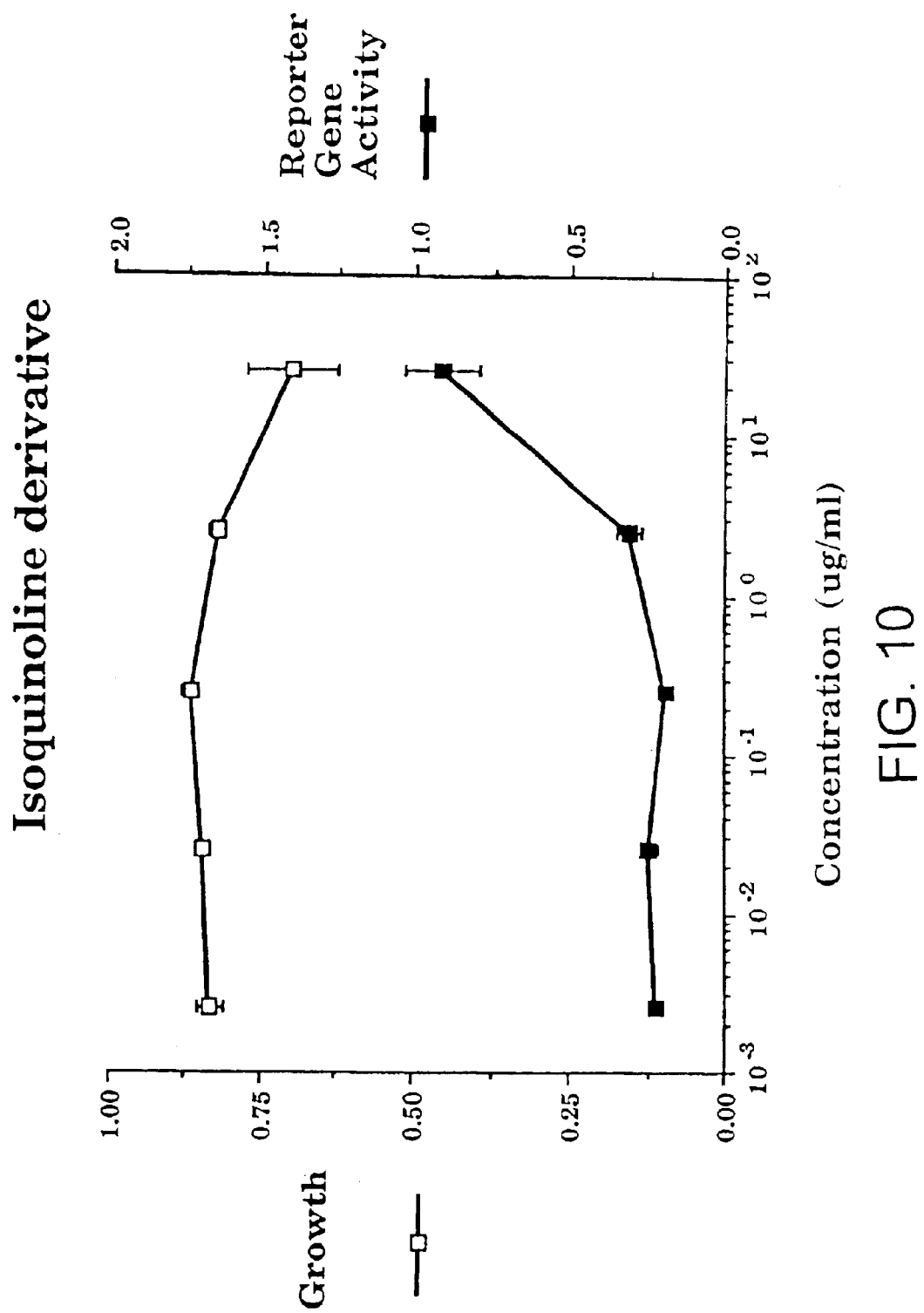
FIG. 10 shows dose-responses of reporter gene activity and growth for 3-(4-t-butylphenyl)-7-isopropyl-N-methylisoquinoline. Nomenclature is as in FIG. 2.

3-(4-t-butylphenyl)-7-isopropyl-N-methylisoquinoline is a D14 reductase inhibitor synthesised as described in EP 052 8553 (Tosoh corporation). Induction of reporter gene activity occurs above concentrations of 1 µg/ml (FIG. 10).

All of the compounds induce observed reporter gene activity at least 3.7 fold; this corresponds to an increase in OD570 from 0.23 to 0.85 during the course of the assay. This difference is easily detectable when the yeast reporter strain is being used in a high throughput screen. The compounds amphotericin B and 5-flucytosine, which are antifungal but do not inhibit sterol biosynthesis, do not induce reporter gene activity in this assay.

The level of reporter gene induction per cell ranges from 5 fold (lovastatin) to 9 fold (terbinafine). The level of reporter gene activity induced by terbinafine may represent the maximal level of reporter gene expression that can be achieved with this reporter construct. The sensitivity of the assay may be improved by either increasing the stimulated level of reporter gene activity, or reducing the basal activity in the absence of sterol biosynthesis inhibition, or a combination of both. The basal level may be affected by growth under different media conditions, and it may be possible to determine a set of growth conditions which, together with the reporter construct described here, improve upon the stimulated-to-basal ratio of reporter gene activity. Alternatively, analysis of the promoter region, followed by the construction of synthetic promoter regions, may improve the sensitivity of the assay.

We find that the assay described here is suitable for use in high throughput screening. When a test run of 2000 compounds from a compound collection were assayed, 3 strong positives (OD change of >0.5) and 5 weak positives (OD change of 0.25–0.5) were obtained. These results suggest that the assay is comparatively selective, and will not result in large numbers of positive compounds for further evaluation. This selectivity is probably attributable to two features of the assay. Firstly, the assay may be described as a "gain-of-function" assay. Thus although the ability of compounds to inhibit a process (sterol biosynthesis) is being assessed, the output used is the stimulation of a process (reporter gene transcription). Compounds which inhibit yeast growth through mechanisms other than inhibition of sterol biosynthesis should not be positive in this assay. Secondly, the reporter gene used displays a low basal activity and a moderately high induced activity. As yet the DNA elements within the promoter which mediate basal and induced reporter gene transcription have yet to be defined. Definition of these elements may allow the construction of more sensitive screens for sterol biosynthesis inhibitors through the removal elements which confer the basal level of transcription, or the multimerisation of elements which mediate the stimulated level of transcription. These approaches, pursued separately, or together, might increase the level of signal (induced reporter gene activity) to noise (basal reporter gene activity).

The reporter yeast strain described is suitable for high throughput screening for three reasons: (i) the reporter strain of yeast displays a low background level of reporter gene activity; (ii) the reporter activity can be significantly increased by incubation with a variety of sterol biosynthesis inhibitors; (iii) a low rate is obtained with compounds from compound collections.

We have not studied the levels of transcription from the endogenous ACoAT gene in the presence of different inhibitors. However, we predict that they will parallel the changes in reporter gene activity described above. Our studies suggest that the differences in acetoacetyl CoA thiolase activities reported by Trocha and Sprinson (op. cit.) are due to differences in gene transcription rather than to post-transcriptional mechanisms, such as alterations in mRNA stability or allosteric or other regulation of enzyme activity. The various compounds which are active in the assay may act by different mechanisms, however it is more likely that they all act by either depletion of ergosterol, or accumulation of an intermediate close to the end of the sterol biosynthesis pathway. Our results also indicate that the DNA seqences which mediate feedback regulation of acetoacetylCoA thiolase gene expression are located within the 0.53 kb promoter fragment used to construct the reporter gene.

What is claimed is:

1. A method for the identification of agents which inhibit sterol biosynthesis which method comprises contacting a test compound with a host cell comprising a DNA sequence which controls expression of a fungal acetoacetyl CoA thiolase gene operably linked to a reporter system such that modulation of sterol biosynthesis in the host cell leads to a detectable change in cell phenotype, and determining whether any such detectable change has occurred.

2. A method as claimed in claim 1 wherein the species used to provide the fungal acetoacetyl-CoA thiolase promoter and/or the host cell is selected from the group consisting of Saccharomyces species, *Saccharomyces cerevisiae, Saccharomyces uvarum, Schizosaccharomyces pombe*, Candida species, *Cryptococcus neoformans, Histoplasma capsulatum, Pneumocystis carinii, Neurospora crassa*, Septoria species, *Magnaporthe grisea*, Aspergillus species, Ustilago species and *Botrylis cinerea*.

3. A method as claimed in claim 1 or claim 2 wherein the host cell also contains mutation(s) or other additional genes which alter the rate of flux through sterol biosynthesis and hence alter the sensitivity of the host cell to sterol biosynthesis inhibitors.

4. A method as claimed in claim 1 or claim 2 wherein the host cell comprises mutation(s) which modify the permeability of the cell wall and/or cell membrane to a test compound or other exogenous agent.

5. A method as claimed in claim 1 wherein the host cell also comprises one or more genes encoding sterol biosynthesis enzyme(s) from other organisms.

6. A method as claimed in claim 1 wherein the reporter system comprises a reporter gene.

7. A host cell which is a fungus transformed with a promoter element which controls expression of a fungal acetoacetyl CoA thiolase gene operably linked to a reporter system such that inhibition of sterol biosynthesis in the host cell leads to a detectable change in cell phenotype.

8. A transformed host cell as claimed in claim 7 wherein the species used to provide the fungal acetoacetyl CoA thiolase promoter and/or the fungus is selected from the group consisting of Saccharomyces species, *Saccharomyces cerevisiae, Saccharomyces uvarum, Schizosaccharomyces pombe*, Candida species, *Cryptococcus neoformans, Histoplasma capsulatum, Pneumocystis carinii, Neurospora crassa*, Septoria species, *Magnaporthe grisea*, Aspergillus species, Ustilago species and *Botrylis cinerea*.

9. A transformed host cell as claimed in claim 7 wherein the host cell also comprises one or more genes encoding sterol biosynthesis enzyme(s) from other organisms.

10. A transformed host cell as claimed in claim 7 wherein the reporter system comprises a reporter gene.

11. A transformed host cell as claimed in one of claims 7–10 wherein the promoter element comprises SEQ ID NO: 1 and a TATA box.

12. A transformed host cell as claimed in one of claims 7–10 wherein the promoter element comprises SEQ ID NO:4.

* * * * *